United States Patent [19]
Mumford

[11] 3,990,880
[45] Nov. 9, 1976

[54] HERBICIDAL ISOBENZOFURANONES

[75] Inventor: Franklin Edward Mumford, Wilmington, Del.

[73] Assignee: E. I. Du Pont de Nemours and Company, Wilmington, Del.

[22] Filed: Nov. 6, 1975

[21] Appl. No.: 629,550

[52] U.S. Cl. .............................. 71/88; 260/343.3 R
[51] Int. Cl.² ................... C07D 307/87; A01N 9/20
[58] Field of Search ................... 260/343.3 R; 71/88

[56] References Cited
OTHER PUBLICATIONS
Roderick et al., "J. Organic Chemistry," vol. 28, No. 8, (1963) 2018–2024.

*Primary Examiner*—Anton H. Sutto

[57] ABSTRACT

This invention relates to herbicidal isobenzofuranones. These compounds may be used for selective weed control in certain crops or for total vegetation control.

9 Claims, No Drawings

HERBICIDAL ISOBENZOFURANONES

BACKGROUND OF THE INVENTION

A number of isoindole-type compounds are known in the prior art.

Recently, in German Offenlegungsschrift 2,165,651, a group of isoindole-1,3-diones which are useful as herbicides was disclosed. The general formula for the isoindole-1,3-diones disclosed in the Offenlegungsschrift is as follows:

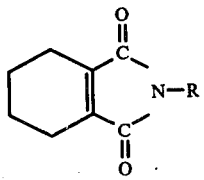

wherein R may be aryl, aralkyl or benzyl optionally substituted with 1 to 5 halogen atoms, hydroxy, nitro, cyano, thiocyanato, carboxy, halogenated alkyl, alkyl, alkoxy, lower alkylthio, or a phenyl grouping; a group having the configuration —O—CH$_2$A may also be substituted therein, wherein A is a phenyl or a naphthyl group, wherein the phenyl group may have one or more substitutions therein, such as halogen atoms, nitro groupings, lower alkyl groupings or lower alkoxy groupings.

Typical of the compounds disclosed in the Offenlegungsschrift is the compound of Example 1:

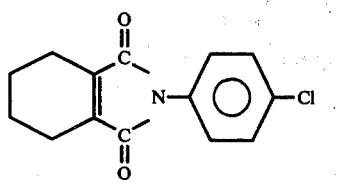

Although the compounds disclosed within the Offenlegungsschrift are active herbicides, the need still exists for herbicides which are more active still. The presence of undesired vegetation is very damaging to useful crops such as rice. In the current world situation, wherein food shortages are acute, it is most important to obtain high yields of valuable crops such as rice. The presence of undesired vegetation results in the loss of a significant portion of such crops due to competition for soil nutrients, water, light, etc. Thus, a need exists for an effective herbicide which will destroy as much of this unwanted vegetation as is possible without causing significant damage to the desired crops, e.g. rice.

According to the instant invention, herbicidal compounds have been discovered which are highly active herbicides and yet cause minimal damage to certain desired crops, e.g. rice.

SUMMARY OF THE INVENTION

This invention relates to novel compounds of Formula I and their compositions, as well as to the method of use of such compounds as herbicides:

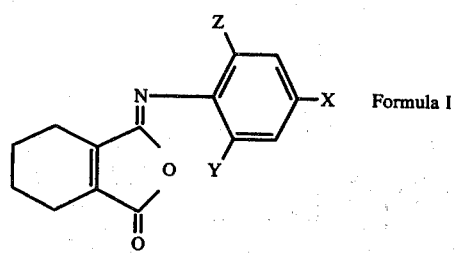

Formula I wherein
X is fluorine, chlorine, or bromine;
Y is hydrogen or fluorine; and
Z is hydrogen or fluorine;
provided that when Y and Z are fluorine, X is fluorine. It is preferred that Z = F. It is more preferred that Z = F and Y = H and X = Cl.

This invention also includes herbicidal compositions containing the above compounds as active ingredients and methods of controlling undesirable vegetation by applying the compounds and/or compositions to the locus of such undesired vegetation.

DESCRIPTION OF THE INVENTION

Synthesis of the Compounds

The compounds of Formula I can be made by the processes described and exemplified below.

The preparation of the subject compounds begins with 2-fluoroaniline and 2'-fluroacetanilide, which can be prepared as described by G. Schiemann and H. G. Baumgarten, Chem. Berichte, 70, 1416 (1937). The process to be utilized in order to form the compounds of the instant invention is as follows:

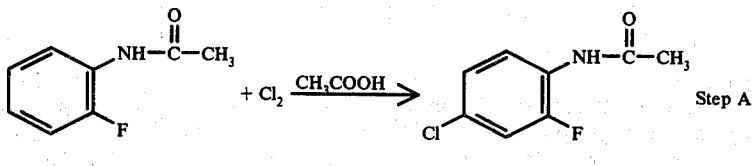

Step A

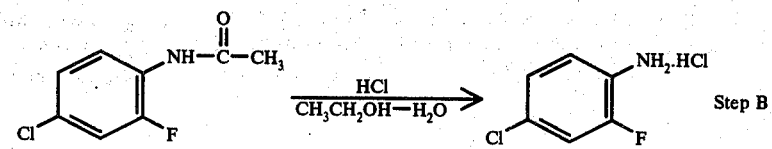

Step B

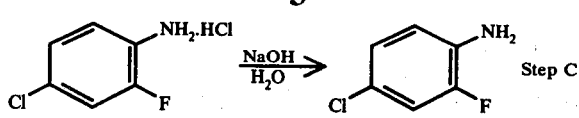

Step C

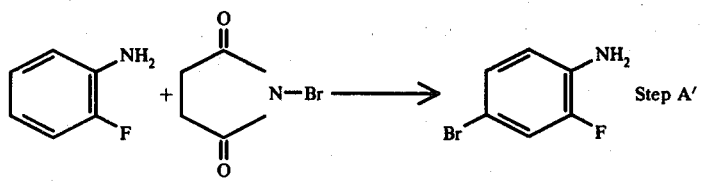

Step A′

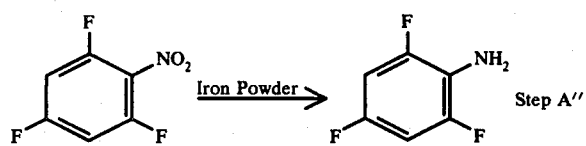

Step A″

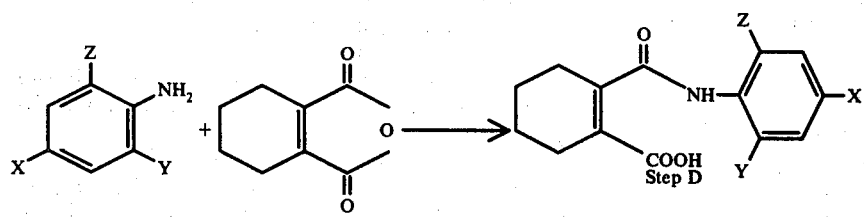

Step D

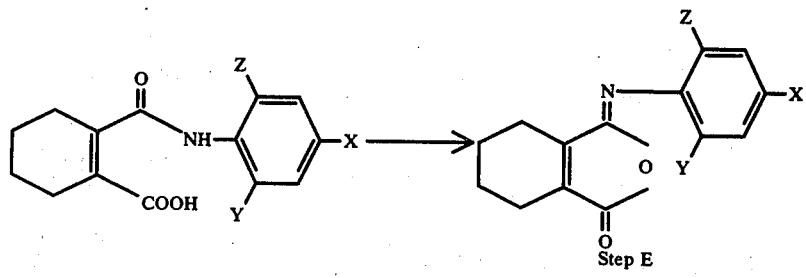

Step E wherein
 X is fluorine, chlorine, or bromine;
 Y is hydrogen or fluorine; and
 Z is hydrogen or fluorine;
provided that when Y and Z are fluorine, X is fluroine.

Step A

The reaction of 2′-fluoroacetanilide and chlorine in acetic acid is well known to those skilled in the art, e.g., W. W. Reed and K. J. P. Orton, J. Chem. Soc., 91, 1543 (1907) for the chlorination of acetanilide to obtain 2′,4′-dichloroacetanilide. The reaction takes place at 25°–30° C over several hours at atmospheric pressure.

Step B

The chlorofluoroacetanilide is refluxed in a mixture of a lower alcohol (50%) and concentrated hydrochloric acid (50%) for several hours at 70°–90° C and atmospheric pressure. The solvent mixture is removed at a reduced pressure of 100 to 300 mm.Hg and 20°–50° C to leave a residue of the hydrochloride salt of 4-chloro-2-fluoroaniline.

Step C

By treatment of an aqueous solution of the hydrochloride salt of 4-chloro-2-fluoroaniline with an alkali metal hydroxide solution, the free 4-chloro-2-fluoroaniline is extracted into a suitable water-immiscible organic solvent such as ethyl ether or methylene chloride. The crude 4-chloro-2-fluoroaniline is isolated by removal of the organic solvent under reduced pressure of 100 to 300 mm.Hg. at 20°–50° C.

Step A'

The reaction of 2-fluoroaniline and N-bromosuccinimide in an inert organic solvent such as methylene chloride is well known to those skilled in the art, e.g., J. B. Wommack et al., J. Het. Chem., 6, 243 (1969). The exothermic reaction takes place at 0° C over several hours. The resulting reaction mixture is washed with water several times and dried with an appropriate drying agent such as anhydrous sodium sulfate. The 4-bromo-2-fluoroaniline is recovered by removal of the organic solvent under reduced pressure of 100 to 300 mm.Hg at 20°–50° C.

Step A''

The synthesis of 2,4,6-trifluoroaniline from 1,3,5-trifluoro-2-nitrobenzene uses the same procedure as that described by G. Schiemann and M. Seyhan [chem. Ber., 70, 2396 (1937)] for the preparation of 2,4-difluoroaniline. The preparation of 1,3,5-trifluoro-2-nitrobenzene is described by V. I. Siele and H. J. Matsuguma, U.S. Dept. Com., Office Serv., P B Rept. 145, 510, p. 1 (1960) [Chem. Abst. 56, 15394C (1962)].

Step D

The mono-, di- or trihaloanilines and 3,4,5,6-tetrahydrophthalic anhydride are refluxed in diethyl ether at temperatures of 35°–37° C. and atmospheric pressure for several hours, e.g. 1 to 20 hours. The 2-arylaminocarbonyl-1-cyclohexene-1-carboxylic acid is isolated by evaporation of the diethyl ether.

Step E

The 2-arylaminocarbonyl-1-cyclohexene-1-carboxylic acid prepared in step D is converted to the corresponding 3-arylimino-4,5,6,7-tetrahydro-1-(3H)-isobenzofuranone by the action of an N,N-dialkyl carbodiimide (such as N,N-dicyclohexylcarbodiimide) in an aprotic solvent (such as dioxane) at ambient temperature over several hours (1–25 hrs). The isobenzofuranone is isolated by first removing the by-product dialkyl urea by filtration, evaporating the filtrate under reduced pressure (100–300 mm. Hg), and fractionating by high pressure liquid chromatography. Alternatively, reaction of the 2-arylaminocarbonyl-1-cyclohexene-1-carboxylic acid with an alkyl haloformate (such as methyl chloroformate) in the presence of a trialkylamine (such as triethylamine) at 0° C in a suitable aprotic solvent (such as methylene chloride) for several hours (1–25 hrs.) followed by washing with water, drying with a suitable dessicant (such as anhydrous sodium sulfate) and evaporation of the solvent under reduced pressure (100–300 mm. Hg) produces the 3-arylimino-4,5,6,7-tetrahydro-1-(3H)-isobenzofuranone.

The compounds which may be prepared by the instant process are as follows:

3-(4-fluorophenylimino)-4,5,6,7-tetrahydro-1-(3H)-isobenzofuranone;

3-(4-chlorophenylimino)-4,5,6,7-tetrahydro-1-(3H)-isobenzofuranone;

3-(4-bromophenylimino)-4,5,6,7-tetrahydro-1-(3H)-isobenzofuranone;

3-(2,4-difluorophenylimino)-4,5,6,7-tetrahydro-1-(3H)-isobenzofuranone;

3-(4-chloro-2-fluorophenylimino)-4,5,6,7-tetrahydro-1-(3H)-isobenzofuranone, m.p. 81°–84° C.;

3-(4-bromo-2-fluorophenylimino)-4,5,6,7-tetrahydro-1-(3H)-isobenzofuranone;

3-(2,4,6-trifluorophenylimino)-4,5,6,7-tetrahydro-1-(3H)-isobenzofuranone.

The following examples further illustrate this method for synthesis of compounds of this invention. All parts are by weight and all temperatures in degrees centigrade unless otherwise indicated.

EXAMPLE 1

Preparation of 2-(4-chloro-2-fluorophenylaminocarbonyl)-1-cyclohexene-1-carboxylic acid A solution of 140 parts of 2'-fluoroacetanilide in 500 parts glacial acetic acid was treated with 71 parts of chlorine during 1 hour at 25°–27° C with ice-water cooling. While stirring for 4 hours at 25°–27° C, 4'-chloro-2'-fluoroacetanilide precipitated. After collecting the product by filtration, the filtrate was poured over 2000 parts of ice. The resulting second portion of product pecipitated was collected by filtration, combined with the first portion and recrystallized from 700 parts of methanol at −45° C. to yield 119 parts of 4'-chloro-2'-fluroacetanilide as white crystals melting at 152°–155° C.

A mixture of 119 parts of 4'-chloro-2'-fluroacetanilide in 475 parts of ethanol and 200 parts of 37% hydrochloric acid was refluxed for 17 hours and the solvent removed under a reduced pressure of 300 mm.Hg. to yield the moist, solid hydrochloride salt of 4-chloro-2-fluoroaniline.

The moist, solid hydrochloride salt of 4-chloro-2-fluoroaniline was cooled in an ice-acetone bath and treated at 10° C with 50% aqueous sodium hydroxide until pH 11 was reached. The resulting two-phase mixture was extracted four times; 500 parts of methylene chloride were used for each extraction. The combined organic extracts were dried with anhydrous sodium sulfate and te solvent removed under reduced pressure of 300 mm.Hg. to leave 89 parts of light brown, oily 4-chloro-2-fluoroaniline, $N_D^{25}$ = 1.5541.

4.8 Parts of 4-chloro-2-fluoroaniline were added to a solution of 5 parts of 3,4,5,6-tetrahydrophthalic anhydride in 150 parts of diethyl ether and stirred for 1.5 hours. The solution was evaporated under reduced pressure of 300 mm. Hg at 25° C to isolate 9 parts of 2-(4-chloro-2-fluorophenylaminocarbonyl)-cyclohexene-1-carboxylic acid as white crystals melting at 91°–93° C.

EXAMPLE 2

Preparation of 3-(4-chloro-2-fluorophenylimino)-4,5,6,7-tetrahydro-1-(3H)-isobenzofuranone A solution of 0.4 parts of N,N-dicyclohexylcarbodiimide in 5 parts of dioxane was added at once to a solution of 0.6 parts of 2-(4-chloro-2-fluorophenylaminocarbonyl)-1-cyclohexene-1-carboxylic acid in 5 parts of dioxane to form a slurry. After stirring the slurry for 1 hour, the resulting solid 1,3-dicyclohexylurea was filtered. The filtrate was evaporated under reduced pressure of 300 mm. Hg at 25° C to a yellow, semisolid residue from which 0.27 parts of 3-(4-chloro-2-fluorophenylimino)-4,5,6,7-tetrahydro-1-(3H)-isobenzofuranone melting at 81°-84° C was isolated after fractionation by high pressure liquid chromatography.

EXAMPLE 3

Preparation of 3-(4-chloro-2-fluorophenylimino)-4,5,6,7-tetrahydro-1-(3H)-isobenzofuranone 1.59 Parts of methyl chloroformate was added dropwise during 15 minutes to a stirred solution of 1.87 parts of triethylamine and 5 parts of 2-(4-chloro-2-fluorophenylaminocarbonyl)-1-cyclohexene-1-carboxylic acid in 200 parts of methylene chloride cooled to 0° C. The reaction mixture was allowed to come to ambient temperature during 1 hour after which it was washed successively with 100 parts of water (twice) and 100 parts of a saturated aqueous sodium chloride solution. After drying with anhydrous sodium sulfate, the solution was evaporated under reduced pressure of 300 mm. Hg at 25° C to 5.6 parts of a yellow semisolid. Analysis of the semisolid by high pressure liquid chromatography indicates the presence of 3-(4-chloro-2-fluorophenylimino)-4,5,6,7-tetrahydro-1-(3H)-isobenzofuranone in 51% concentration.

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of a) about 0.1% to 20% surfactant(s) and b) about 1% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et. al., "Handbook of Insecticide Dust Diluents and Carriers," 2nd. Edn., Dorland Books, Caldwell, N. J. The more absorptive diluents are preferred for wettable powders and the denser ones for dusts. Typical liquid diluents and solvents are described in Marsden, "Solvents Guide," 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual," Allured Publ. Corp., Ridgewood, New Jersey, as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," *Chemical Engineering*, Dec. 4, 1967, pp. 147ff. and "Perry's Chemical Engineer's Handbook," 4th. Edn., McGraw-Hill, N.Y., 1963. pp. 8–59ff.

For further information regarding the art of formulation, see for example:
- H. M. Loux, U.S. Pat. No. 3,235,361, Feb. 15, 1966, Col. 6, Line 16 through Col. 7, Line 19 and Examples 10 through 41.
- R. W. Luckenbaugh, U.S. Pat. No. 3,309,192, Mar. 14, 1967, Col. 5 Line 43 through Col. 7 Line 62 and Ex. 8, 12, 15, 39, 41, 52, 53, 58, 132, 138–140, 162–164, 166, 167, 169—182.
- H. Gysin and E. Knusli, U.S. Pat. No. 2,891,855, June 23, 1959, Col. 3 Line 66 through Col. 5 Line 17 and Examples 1–4.
- G. C. Klingman, "Weed Control as a Science," John Wiley & Sons, Inc., New York, 1961 pp. 81–96.
- J. D. Fryer and S. A. Evans, "Weed Control Handbook," 5th Edn. Blackwell Scientific Publications, Oxford, 1968, pp. 101–103.

The compounds of Formula I can be combined with other herbicides and are particularly useful in combination with bromacil [3-(sec-butyl)-5-bromo-6-methyluracil], diuron[3-(3,4-dichlorophenyl)-1,1-dimethylurea], paraquat [1,1'-dimethyl-4,4'-bipyridinum ion], m-(3,3-dimethylureido)-phenyl tert-butylcarbamate, 4-amino-6-tert-butyl-3-methylthio-as-triazin-5(4H)-one, and the s-triazines such as 2-chloro-4-ethylamino-6-isopropylamino-s-triazine, for controlling a broad spectrum of weeds.

EXAMPLE 4

Granule

| | |
|---|---|
| 3-(2,4-difluorophenylimino)-4,5,6,7-tetrahydro-1-(3H)-isobenzofuranone | 10% |
| attapulgite granules (low volative matter, 0.71/0.30 mm; U.S.S. No. 25–50 sieves) | 90% |

The active ingredient is warmed to approximately 90° C and sprayed upon dedusted and pre-warmed attapul-

EXAMPLE 5

Oil Suspension

| | |
|---|---|
| 3-(2,4-difluorophenylimino)-4,5,6,7-tetrahydro-1-(3H)-isobenzofuranone | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 6

Solution

| | |
|---|---|
| 3-(2,4,6-trifluorophenylimino)-4,5,6,7-tetrahydro-1-(3H)-isobenzofuranone | 30% |
| dimethylformamide | 70% |

The ingredients are combined and stirred to produce a solution, which can be used for low volume applications.

EXAMPLE 7

Emulsifiable Concentrates

| | |
|---|---|
| 3-(4-chloro-2-fluorophenylimino)-4,5,6,7-tetrahydro-1-(3H)-isobenzofuranone | 30% |
| blend of oil soluble sulfonates and polyoxyethylene ethers | 4% |
| xylene | 66% |

The ingredients are combined and stirred with gentle warming, e.g. 50° C. to speed solution. A fine screen filter is included in the packaging operation to insure the absence of any extraneous material in the product.

EXAMPLE 8

Wettable Powder

| | |
|---|---|
| 3-(4-chloro-2-fluorophenylimino)-4,5,6,7-tetrahydro-1-(3H)-isobenzofuranone | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

EXAMPLE 9

Aqueous Suspension

| | |
|---|---|
| 3-(4-bromo-2-fluorophenylimino)-4,5,6,7-tetrahydro-1-(3H)-isobenzofuranone | 50.0%11 |
| polyacrylic acid thickeners | 0.3% |
| dodecylphenol polyethylene glycol ether | 0.5% |
| disodium phosphate | 1.0% |
| monosodium phosphate | 0.5% |
| polyvinyl alcohol | 1.0% |
| pentachlorophenol | 0.4% |
| water | 46.3% |

The ingredients are ground together in a cooled sand mill to produce particles essentially all under five microns in size.

EXAMPLE 10

High Strength Concentrate

| | |
|---|---|
| 3-(2,4,6-trifluorophenylimino)-4,5,6,7-tetrahydro-1-(3H)-isobenzofuranone | 98.5% |
| silica aerogel | 0.5% |
| synthetic amorphous fine silica | 1.0% |

The ingredients are blended to produce a high strength concentrate essentially all passing a U.S.S. No. 50 sieve (0.3 mm. openings). This material may then be formulated in a variety of ways.

Utility

The compounds of Formula I are useful for the selective preemergence weed control of undesired vegetation in crops such as rice, soybeans and peanuts. These compounds also have utility for the postemergence control of weeds in certain crops, for example, soybeans. Furthermore, compounds of this invention can be used as directed treatments for the pre/post-emergence control of weeds in various crops including soybeans, peanuts, garden beans and row-planted rice.

The compounds of this invention are useful for the control of weeds in transplanted crops such as rice, tobacco, tomatoes, sweet potatoes, cabbages, lettuce, celery, peppers, and eggplant. The treatment may be applied to the soil surface prior to transplanting and the crop transplanted through the treated soil or it may be soil incorporated prior to transplanting and the crop set in the treated soil. Rates used will vary from ⅛ to 1-½ kg/ha depending on the crop, the soil type, compound and method of application. One skilled in the art may select the rate for any given situation. In addition, these compounds are useful wherever general weed control is required, such as industrial sites, railroad and utility rights-of-way, along fences, building foundations, parking and storage lots, etc.

The precise amount of the compounds of Formula I to be used in any given situation will vary according to the particular end result desired, the use involved, the plant and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.125 to about 20 kilograms, preferably about 0.25 to about 10 kilograms, per hectare. The lower rates in this range will generally be selected on lighter soils, soils low in organic matter content, for selective weed control in crops, or in situations where maximum persistence is not necessary.

Herbicidal activity of a compound of this invention was demonstrated in a greenhouse test. The procedure of this test was as follows:

Seeds of crabgrass (Digitaria spp.), barnyardgrass Echinochloa crusgalli), wild oats (Avena fatua), Cassia tora, morningglory (Ipomoea spp.), cocklebur (Xanthium spp.), sorghum, corn, soybean, rice, wheat and nutsedge (Cyperus rotundus) tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass, with two leaves, barnyardgrass with two leaves, wild oats with one leaf, Cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days, then all species were compared to controls and visually rated for response to treatment. A quantitative rating was made on a scale of 0 to 10; a rating of 10 means complete kill, a rating of 0 means no injury. A qualitative rating for type of injury was also made; the letter "B" indicates foliage burn, "E" denotes emergence inhibition, "C" means chlorosis/necrosis, "G" indicates growth retardation and "H" stands for formative effects. "X" means axillary stimulation.

TABLE

| | COMPOUND 3-(4-chloro-2-fluorophenylimino)-4,5,6,7-tetrahydro-1-(3H)-isobenzofuranone |
|---|---|
| POST EMERGENCE | |
| Kg. Ha. | 0.4 |
| Bush Bean | 10B |
| COTTON | 10B |
| MORNING GLORY | 9B |
| COCKLEBUR | 10B |
| CASSIA | 6B |
| NUTSEDGE | 5B |
| CRABGRASS | 9B |
| BARNYARD GRASS | 8B |
| WILD OATS | 7B |
| WHEAT | 7B |
| CORN | 9B |
| SOYBEAN | 9B 5X |
| RICE | 9B |
| SORGHUM | 9B |
| PRE-EMERGENCE | |
| MORNING GLORY | 6G |
| COCKLEBUR | 10E |
| CASSIA | 10C |
| NUTSEDGE | O |
| CRABGRASS | 7H |
| BARNYARD GRASS | 8C |
| WILD OATS | 2C |
| WHEAT | 2C |
| CORN | 1C 5G |
| SOYBEAN | 4G |
| RICE | 2C |
| SORGHUM | 2C |

From the above data, it is seen that a representative compound of the instant invention is a superior herbicide.

What is claimed is:
1. A compound of the formula

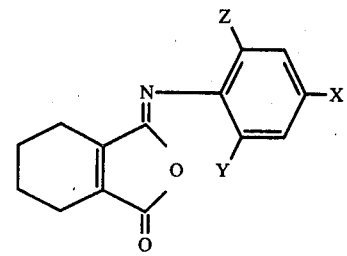

wherein
X is fluorine, chlorine or bromine;
Y is hydrogen or fluorine; and
Z is hydrogen or fluorine;
provided that when Y and Z are fluorine, X is fluorine.

2. A compound of claim 1 wherein X is chlorine.
3. A compound of claim 1 wherein X is chlorine; Y is hydrogen, and Z is fluorine.
4. A composition for the control of undesirable vegetation consisting essentially of a compound of claim 1 and at least one of (a) a surface-active agent and (b) a solid or liquid diluent.
5. A composition for the control of undesirable vegetation consisting essentially of a compound of claim 2 and at least one of (a) a surface-active agent and (b) a solid or liquid diluent.
6. A composition for the control of undesirable vegetation consisting essentially of a compound of claim 3 and at least one of (a) a surface-active agent and (b) a solid or liquid diluent.
7. A method for the control of undesirable vegetation comprising applying to the locus of such undesired vegetation, a herbicidally effective amount of the compound of claim 1.
8. A method for the control of undesirable vegetation comprising applying to the locus of such undesired vegetation, a herbicidally effective amount of the compound of claim 2.
9. A method for the control of undesirable vegetation comprising applying to the locus of such undesired vegetation, a herbicidally effective amount of the compound of claim 3.

* * * * *